US010660637B2

(12) United States Patent
Taylor et al.

(10) Patent No.: US 10,660,637 B2
(45) Date of Patent: May 26, 2020

(54) SUTURING SYSTEM

(71) Applicant: Cypris Medical, Inc., Chicago, IL (US)

(72) Inventors: Richard Keith Taylor, Fall City, WA (US); Amanda Kay Woodcock, Seattle, WA (US); Adam David Hensel, Gahanna, OH (US)

(73) Assignee: Cypris Medical, Inc., Chicago, IL (US)

( * ) Notice: Subject to any disclaimer, the term of this patent is extended or adjusted under 35 U.S.C. 154(b) by 144 days.

(21) Appl. No.: 15/947,612

(22) Filed: Apr. 6, 2018

(65) Prior Publication Data
US 2019/0307445 A1 Oct. 10, 2019

(51) Int. Cl.
A61B 17/04 (2006.01)
A61B 17/06 (2006.01)
A61B 17/00 (2006.01)

(52) U.S. Cl.
CPC .... A61B 17/0485 (2013.01); A61B 17/06066 (2013.01); A61B 17/0469 (2013.01); A61B 17/06166 (2013.01); A61B 2017/00349 (2013.01)

(58) Field of Classification Search
CPC ............ A61B 17/0485; A61B 17/0469; A61B 2017/0409; A61B 17/06066; A61B 2017/00349; A61B 17/0482; A61B 17/062; A61B 2017/00792; A61B 2017/06019; A61B 2017/06042; A61B 2017/306
USPC .......................................... 606/144
See application file for complete search history.

(56) References Cited

U.S. PATENT DOCUMENTS

| 3,206,217 | A | 9/1965 | Shepard et al. |
| 4,210,148 | A | 7/1980 | Stivala |
| 4,268,481 | A | 5/1981 | Souvaniemi et al. |
| 4,373,530 | A | 2/1983 | Kilejian |
| 4,841,888 | A | 6/1989 | Mills et al. |
| 4,950,283 | A | 8/1990 | Dzubow et al. |
| 5,507,754 | A | 4/1996 | Green et al. |
| 5,525,302 | A | 6/1996 | Astle |
| 5,549,617 | A | 8/1996 | Green et al. |
| 5,792,163 | A | 8/1998 | Swain et al. |
| 5,797,927 | A | 8/1998 | Yoon |
| 5,908,426 | A * | 6/1999 | Pierce .................. A61B 17/062 606/139 |
| 5,984,932 | A | 11/1999 | Yoon |
| 6,155,989 | A | 12/2000 | Collins |
| 6,533,796 | B1 | 3/2003 | Sauer et al. |

(Continued)

FOREIGN PATENT DOCUMENTS

WO 2004/062466 7/2004

OTHER PUBLICATIONS

Covidien. SILS™ Stitch Articulating Suturing Device. Product Sheet, www.covidiet.com, originally downloaded Jan. 6, 2016, 2 pages.

(Continued)

Primary Examiner — Elizabeth Houston
Assistant Examiner — Alyssa M Keane
(74) Attorney, Agent, or Firm — Craig R. Miles; CR Miles P.C.

(57) ABSTRACT

A suturing system including apparatus and methods for disposing stitches in a substrate comprising a thread carrier which inserts a thread in the substrate at a first location and withdraws the thread from the substrate at a second location.

18 Claims, 16 Drawing Sheets

(56) References Cited

U.S. PATENT DOCUMENTS

| | | |
|---|---|---|
| 6,997,931 B2 | 2/2006 | Sauer et al. |
| 7,060,079 B2 | 6/2006 | Wulc et al. |
| 7,220,266 B2 | 5/2007 | Gambale |
| 7,517,356 B2 | 4/2009 | Heinrich |
| 7,731,727 B2 | 1/2010 | Sauer |
| 7,780,684 B2 | 8/2010 | Wulc et al. |
| 8,075,573 B2 | 12/2011 | Gambale et al. |
| 8,177,794 B2 | 5/2012 | Cabrera et al. |
| 8,177,797 B2 | 5/2012 | Shimoji et al. |
| 8,226,665 B2 | 7/2012 | Cohen |
| 8,246,637 B2 | 8/2012 | Viola et al. |
| 8,286,847 B2 | 10/2012 | Taylor |
| 8,292,886 B2 | 10/2012 | Kerr et al. |
| 8,292,905 B2 | 10/2012 | Taylor et al. |
| 8,292,906 B2 | 10/2012 | Taylor et al. |
| 8,313,509 B2 | 11/2012 | Kostrzewski |
| 8,337,515 B2 | 12/2012 | Viola et al. |
| 8,372,090 B2 | 2/2013 | Wingardner et al. |
| 8,403,837 B2 | 3/2013 | Okoniewski |
| 8,413,869 B2 | 4/2013 | Heinrich |
| 8,465,499 B2 | 6/2013 | Onuki et al. |
| 8,475,453 B2 | 7/2013 | Marczyk et al. |
| 8,490,851 B2 | 7/2013 | Blier et al. |
| 8,496,674 B2 | 7/2013 | Cabrera et al. |
| 8,506,581 B2 | 8/2013 | Wingardner, III et al. |
| 8,628,545 B2 | 1/2014 | Cabrera et al. |
| 8,636,752 B2 | 1/2014 | Cabrera et al. |
| 8,641,729 B2 | 2/2014 | Filipi et al. |
| 8,721,640 B2 | 5/2014 | Taylor et al. |
| 8,747,424 B2 | 6/2014 | Taylor et al. |
| 8,906,041 B2 | 12/2014 | Chu |
| 8,968,339 B2 | 3/2015 | Malkowski |
| 8,968,340 B2 | 3/2015 | Chowaniec et al. |
| 8,968,342 B2 | 3/2015 | Wingardner, III et al. |
| 9,113,860 B2 | 8/2015 | Viola et al. |
| 9,149,270 B2* | 10/2015 | Fogel ............... A61B 17/0469 |
| 9,204,924 B2 | 12/2015 | Marczyk et al. |
| 9,326,770 B2 | 5/2016 | Shelton, IV et al. |
| 2002/0119177 A1 | 8/2002 | Bowman et al. |
| 2003/0208209 A1* | 11/2003 | Gambale .......... A61B 17/00234 |
| | | 606/144 |
| 2004/0015177 A1 | 1/2004 | Chu |
| 2004/0034371 A1 | 2/2004 | Lehman et al. |
| 2004/0236353 A1 | 11/2004 | Bain et al. |
| 2005/0251153 A1* | 11/2005 | Sakamoto .......... A61B 17/0469 |
| | | 606/139 |
| 2006/0036232 A1 | 2/2006 | Primavera et al. |
| 2006/0085016 A1 | 4/2006 | Eremia |
| 2008/0147096 A1 | 6/2008 | Azonian et al. |
| 2009/0018580 A1 | 1/2009 | Wulc |
| 2010/0016868 A1 | 1/2010 | Kim |
| 2010/0137888 A1 | 6/2010 | Wulc et al. |
| 2010/0249498 A1 | 9/2010 | Wingardner et al. |
| 2011/0082347 A1 | 4/2011 | Okoniewski |
| 2012/0029536 A1* | 2/2012 | Dicesare ............ A61B 17/0469 |
| | | 606/145 |
| 2012/0215235 A1 | 8/2012 | Fogel |
| 2013/0035688 A1 | 2/2013 | Kerr et al. |
| 2013/0172685 A1 | 7/2013 | Okoniewski |
| 2014/0012292 A1 | 1/2014 | Stewart et al. |
| 2014/0114309 A1 | 4/2014 | Payne et al. |
| 2014/0163375 A1 | 6/2014 | Wasielewski |
| 2014/0371760 A1 | 12/2014 | Menn |
| 2016/0338691 A1* | 11/2016 | Weber ................ A61B 17/0469 |

OTHER PUBLICATIONS

Covidien. V-Loc™ Wound Closure Reload for Use With Endo Stitch™ and SILS™ Stitch Suturing Devices. Product Sheet, www.covidiet.com, originally downloaded Jan. 6, 2016, 28 pages.

Eremia et al. Novel Face-Lift Suspension Suture and Inserting Instrument: Use of Large Anchors Knotted into a Suture with Attached Needle and Inserting Device Allowing for Single Entry Point Placement of Suspension Suture. Preliminary Report of 20 Cases with 6-to 12-Month Follow-Up. Dermatol Surg., Mart 2006, 32(3):335-45.

PCT International Patent Application No. PCT/US07/21449, filed Oct. 5, 2007.

U.S. Appl. No. 60/958,474, filed Jul. 6, 2007.

U.S. Appl. No. 60/923,980, filed Apr. 17, 2007.

U.S. Appl. No. 60/923,804, filed Apr. 16, 2007.

U.S. Appl. No. 60/849,561, filed Oct. 5, 2006.

U.S. Appl. No. 60/849,508, filed Oct. 5, 2006.

U.S. Appl. No. 60/849,562, filed Oct. 5, 2006.

U.S. Appl. No. 62/473,271, filed Mar. 17, 2017.

U.S. Appl. No. 15/917,217, filed Mar. 9, 2018.

PCT International Patent Application No. PCT/US18/21942, filed Mar. 12, 2018.

PCT International Patent Application No. PCT/US18/37406; International Search Report and Written Opinion of the International Searching Authority dated Sep. 13, 2018, 10 pages.

PCT International Patent Application No. PCT/US18/27173; International Search Report and Written Opinion of the International Searching Authority dated Jun. 29, 2018, 8 pages.

PCT International Patent Application No. PCT/US18/27173, filed Apr. 11, 2018.

PCT International Patent Application No. PCT/US18/21942; International Search Report and Written Opinion of the International Searching Authority dated May 24, 2018, 13 pages.

U.S. Appl. No. 15/917,217; Office Action dated Sep. 8, 2019.

* cited by examiner

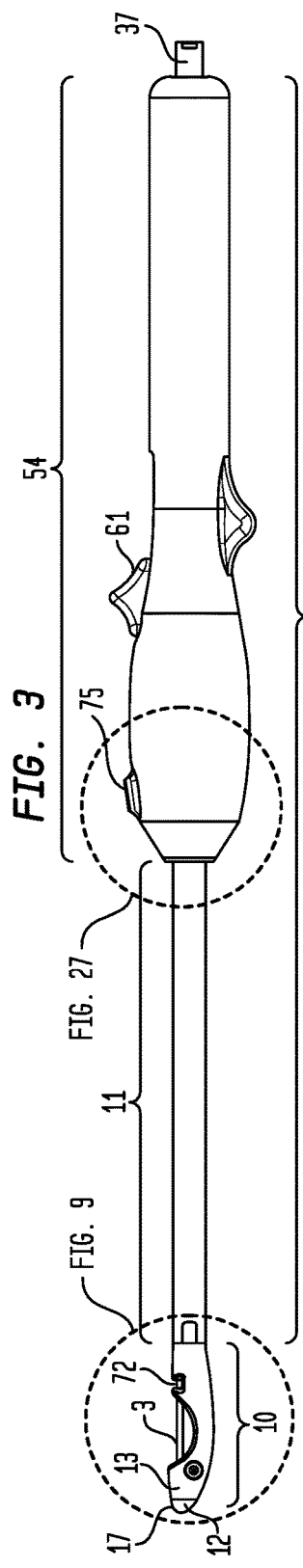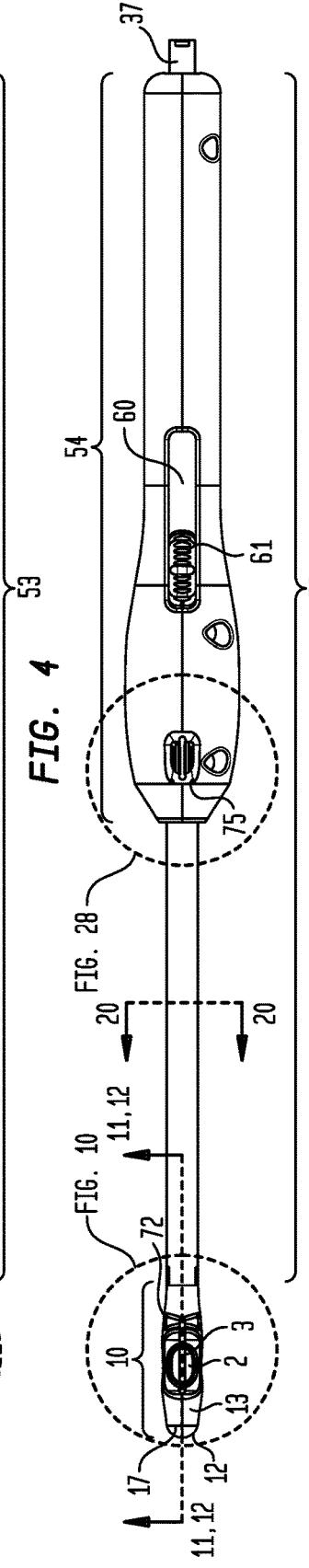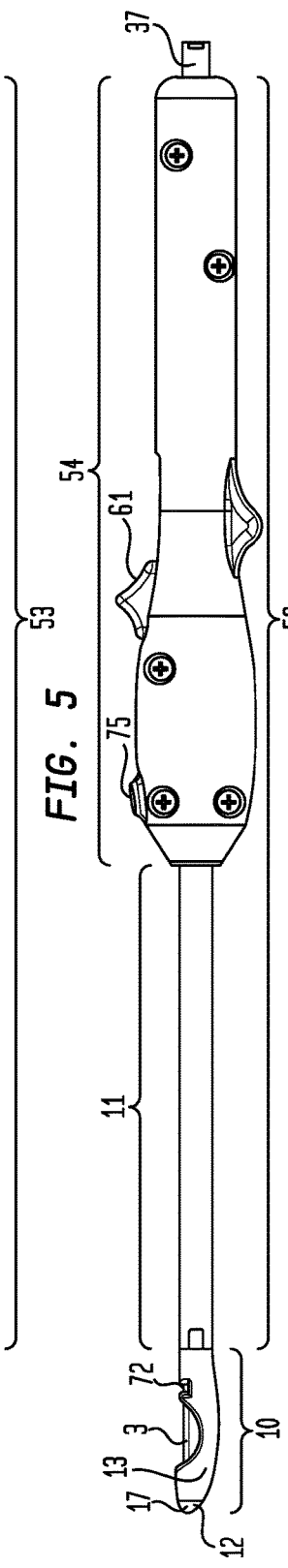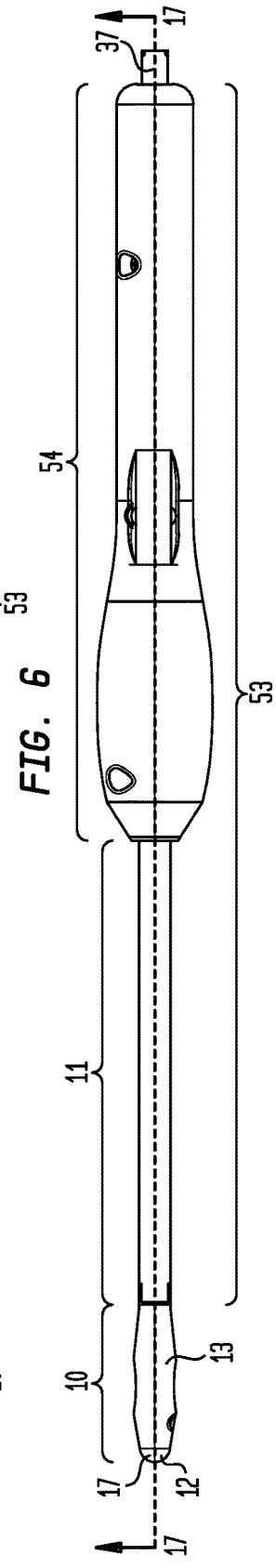

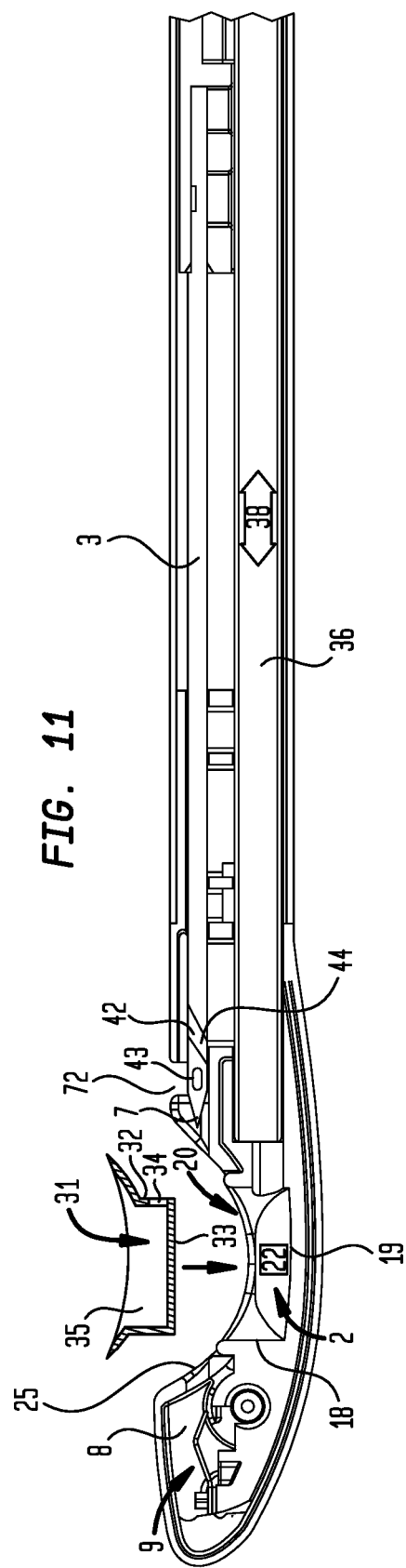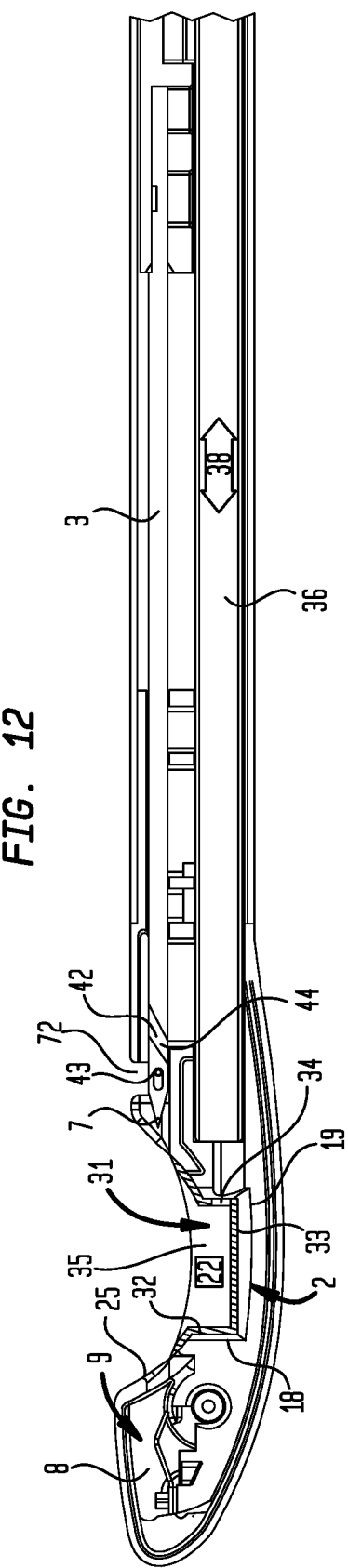

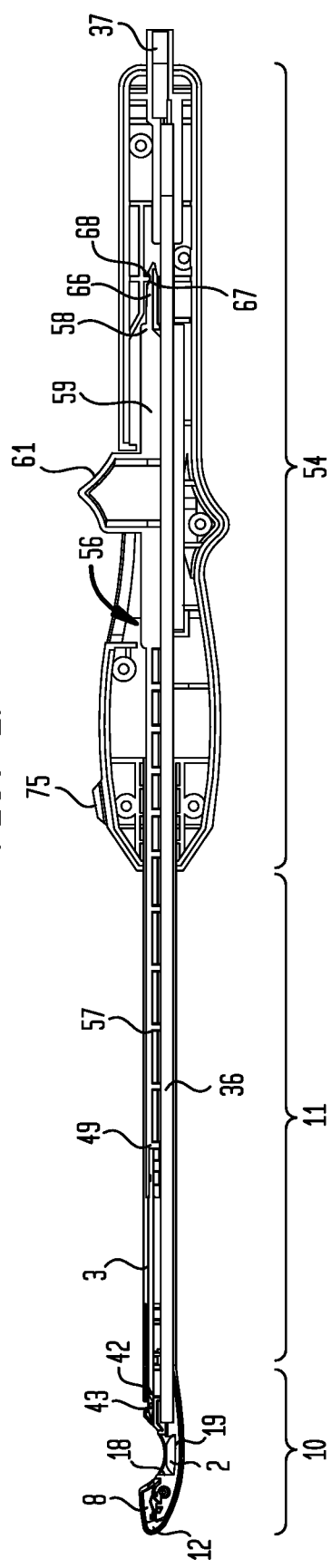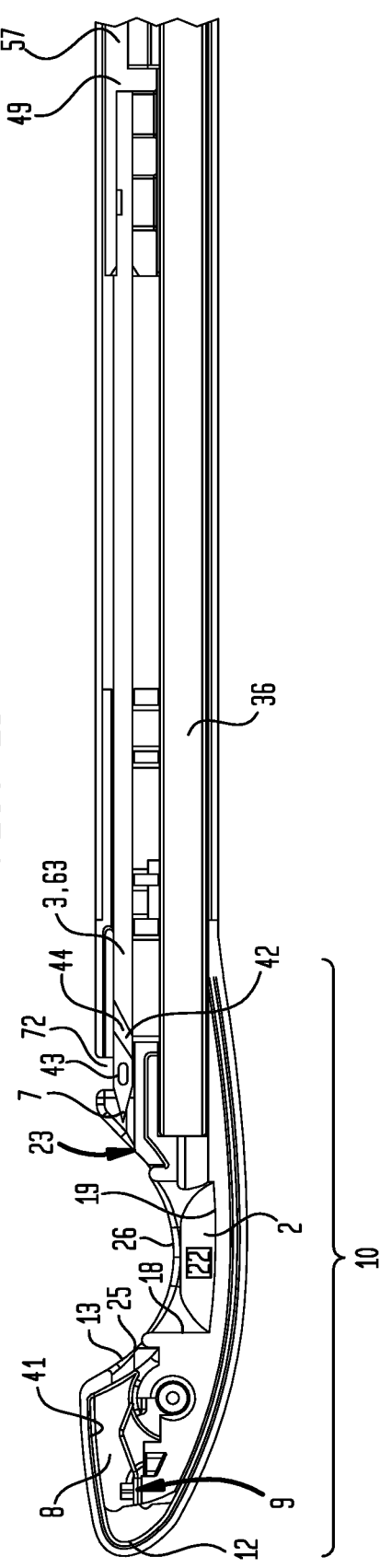

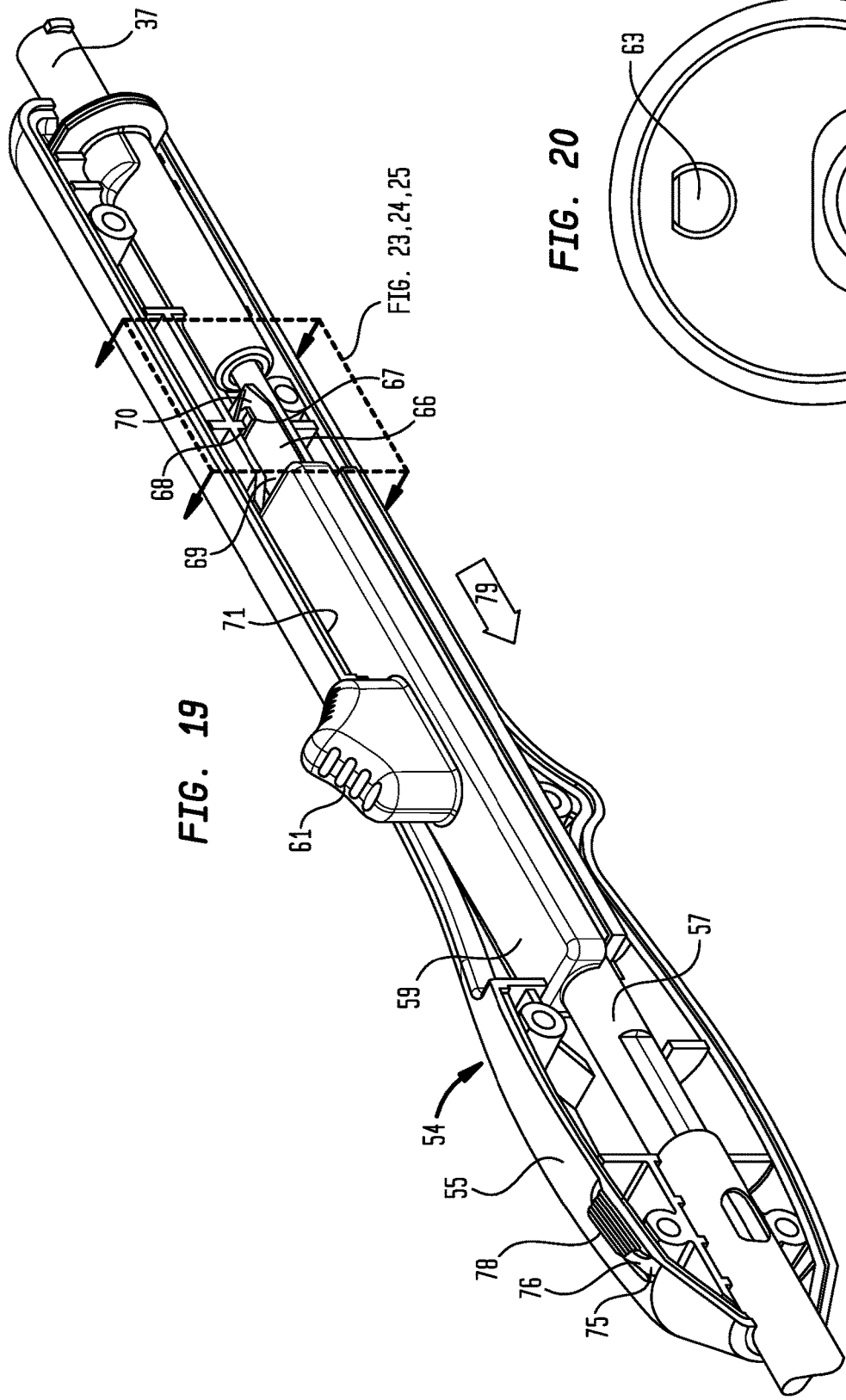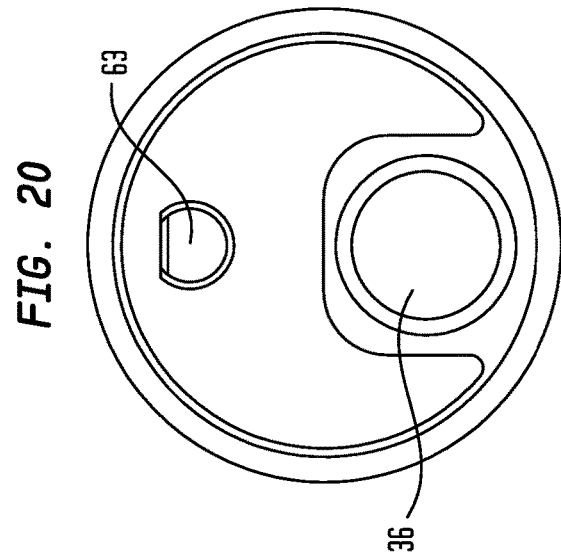

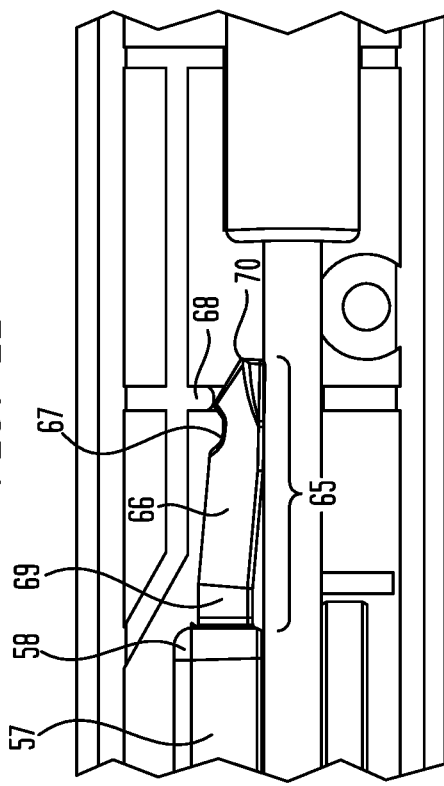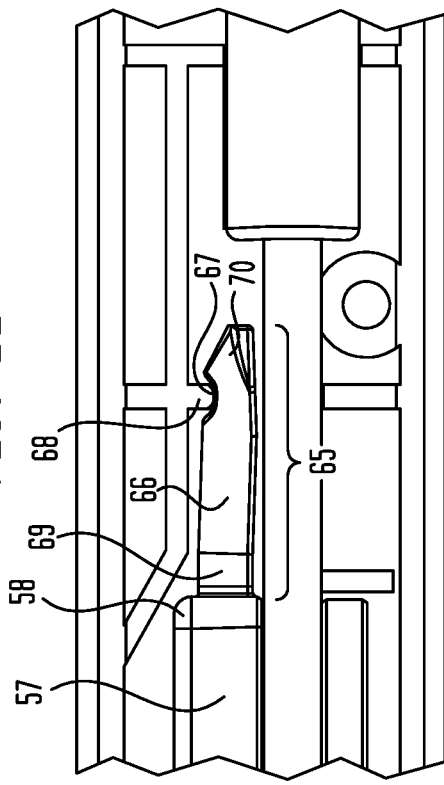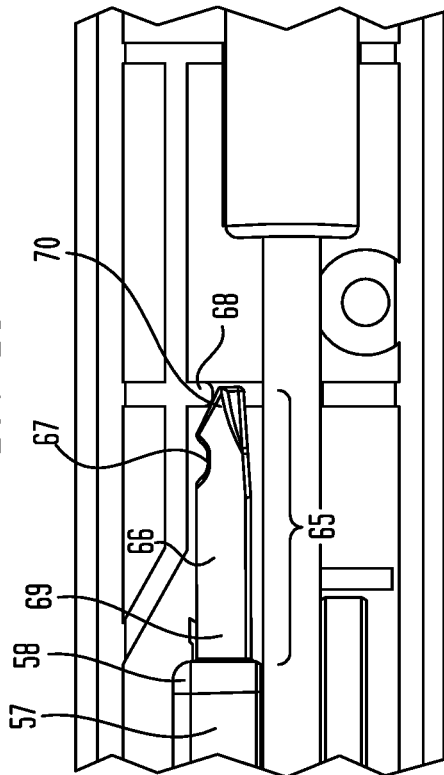

US 10,660,637 B2

SUTURING SYSTEM

I. BACKGROUND

A suturing system including apparatus and methods for disposing stitches in a substrate comprising a thread carrier which inserts a thread in the substrate at a first location and withdraws the thread from the substrate at a second location.

II. SUMMARY OF THE INVENTION

Accordingly, a broad object of the present invention is to provide an apparatus including one or more of a suturing probe including a thread capture chamber disposed adjacent a substrate capture chamber having a chamber port open to a suturing probe external surface and a thread carrier slidingly engaged to the suturing probe which passes outside of the substrate capture chamber into the thread capture chamber.

Another broad object of the present invention is to provide a method for making an apparatus including one or more of disposing in a suturing probe a thread capture chamber adjacent a substrate capture chamber having a chamber port opening to a suturing probe external surface and slidingly engaging a thread carrier in the suturing probe, the thread carrier passing outside of the substrate capture chamber into the thread capture chamber.

Another broad object of the present invention is to provide a method of using an apparatus including one or more of capturing a substrate in a substrate capturing chamber of a suturing probe and driving a thread carrier in the suturing probe toward a thread capture chamber adjacent to the substrate capture chamber, the thread carrier passing through the substrate into the thread capture chamber outside the substrate capture chamber.

Naturally, further objects of the invention are disclosed throughout other areas of the specification, drawings, photographs, and claims.

III. A BRIEF DESCRIPTION OF THE DRAWINGS

FIG. 3 is a first side elevation view of an embodiment of the suturing apparatus.

FIG. 4 is a top plan view of an embodiment of the suturing apparatus.

FIG. 5 is a second side elevation view of an embodiment of the suturing apparatus.

FIG. 6 is a bottom plan view of an embodiment of the suturing apparatus.

FIG. 11 is a cross section view 11-11 as shown in FIG. 4 of a particular embodiment of a suturing probe and a substrate capture chamber insert removed from a substrate capture chamber.

FIG. 12 is a cross section view 12-12 as shown in FIG. 4 of a particular embodiment of a suturing probe and a substrate capture chamber insert coupled to a substrate capture chamber.

FIG. 17 is a cross section view of a particular embodiment of a suturing apparatus as shown in FIG. 4.

FIG. 18 is an enlarged view of a portion of the cross section of a particular embodiment of a suturing probe shown in FIG. 17.

FIG. 19 is an enlarged perspective view of a portion of the cross section of a particular embodiment of a handle shown in FIG. 17.

FIG. 20 is an enlarged view of a cross section 20-20 of a particular embodiment of a tubular member shown in FIG. 4.

FIG. 21 is an enlarged cross section view of a particular embodiment of an arrest assembly in a thread carrier first position.

FIG. 22 is an enlarged cross section view of a particular embodiment of an arrest assembly between a thread carrier first position and a thread carrier second position.

FIG. 23 is an enlarged cross section view of a particular embodiment of an arrest assembly in a thread carrier second position.

IV. DETAILED DESCRIPTION OF THE PREFERRED EMBODIMENTS

Figure 1:
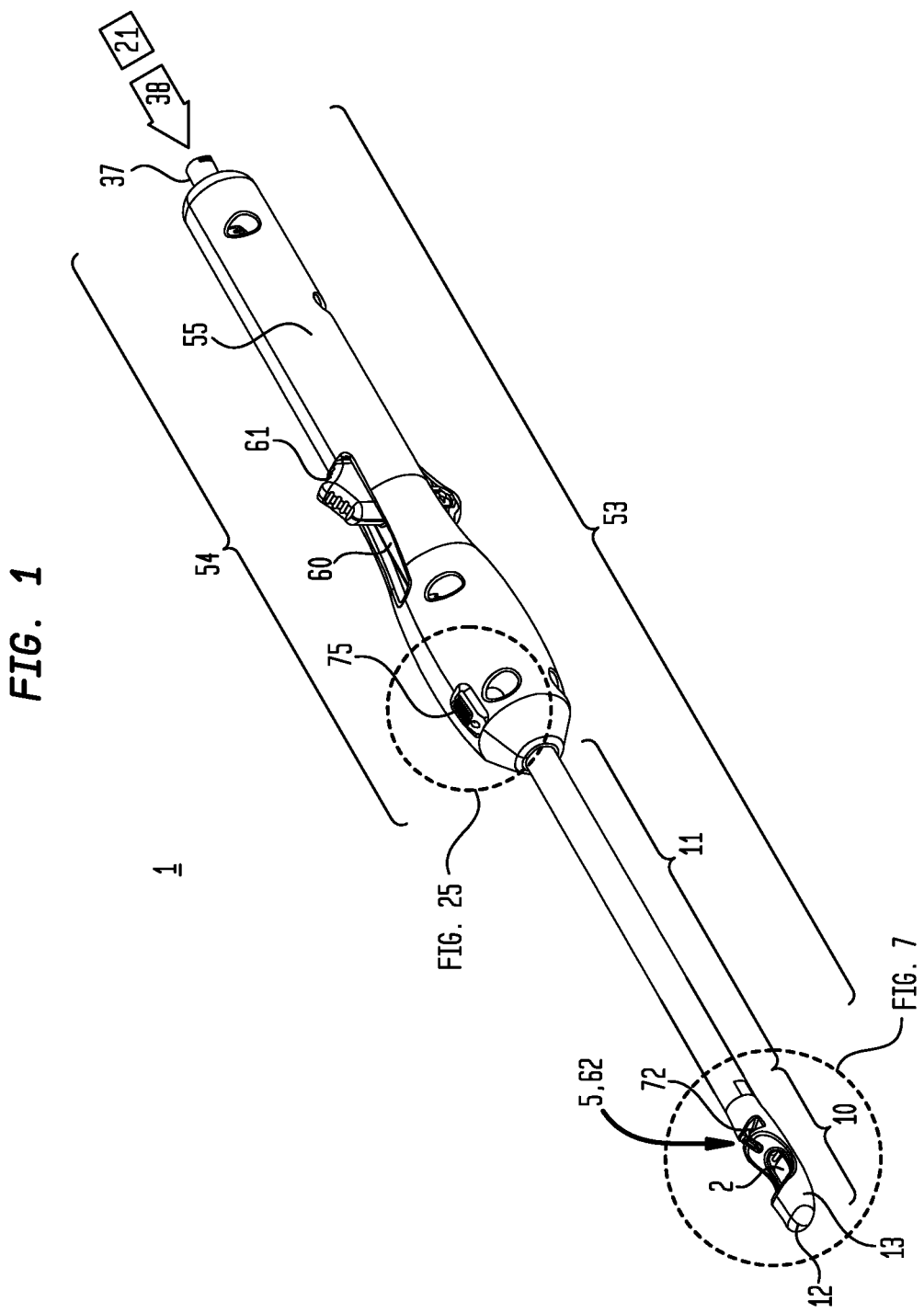
FIG. 1 is a first perspective view of an embodiment of the suturing apparatus having a thread carrier in a retracted condition.

Generally referring to FIGS. 1 through 31, embodiments of a suturing apparatus (1) including a substrate capture chamber (2) and a thread carrier (3) carrying a thread (4) which axially moves between a retracted condition (5) toward an extended condition (6) in which a thread carrier terminal end (7) of the thread carrier (3) passes outside of the substrate capture chamber (2) into a thread capture chamber (8) to engage a thread capture assembly (9) which captures the thread (4) to generate a thread loop upon return of the thread carrier (3) toward the retracted condition (5).

Now referring primarily to FIGS. 1 through 10, embodiments of the suturing apparatus (1) can include a suturing probe (10). The suturing probe (10) can outward axially extend from a tubular member (11) to terminate in a probe tip (12). The suturing probe external surface (13) can, but need not necessarily, be configured as an extension of the external dimensions of the tubular member (11) allowing the probe tip (12) to pass through body openings (14) such as natural body openings or incisions to engage a substrate (15) (as shown in the illustrative example of FIGS. 33A through 33E) such as skin, fascia, fat, or muscle. While particular examples of a substrate (15) include tissue (16) including human or animal tissue, this description is not intended to preclude the capture of substrates (15) other than human or animal tissue, including as illustrative examples, cadaver tissue, simulants of tissue, tissue models, elastomer components, plastic or natural fabrics, or the like.

Again referring primarily to FIGS. 1 through 10, in particular embodiments, the suturing probe (10) can have a generally cylindrical suturing probe external surface (13) terminating in a hebetated probe tip (12). As to particular embodiments, the suturing probe external surface (13) can include a tapered, beveled, or sloped surface approaching the probe tip (12) to reduce dimensions at the probe tip (12). There can be an advantage in having a sloped, tapered or inclined probe face (17) as it allows the suturing probe (10) additional ingress into a substrate (15) such as animal tissues with a lesser amount of tissue dissection or trauma.

Again, referring primarily to FIGS. 1 through 10, in particular embodiments, a substrate capture chamber (2) can be disposed in the suturing probe (10). The substrate capture chamber (2) can include a chamber sidewall (18) which couples in opposed fixed relation a chamber bottom (19) a distance from said chamber port (20) open to the suturing probe external surface (13). In particular embodiments, the vertical chamber side wall (18) can define a periphery of greater circumference than the periphery of the chamber port (20). In particular embodiments, the substrate capture chamber (2) can, but need not necessarily, be fluidically coupled to a vacuum source (21) operable to generate a reduced chamber pressure (22) in the substrate capture chamber (2) sufficient to capture, draw, or dispose a substrate (15) into the substrate capture chamber (2).

In particular embodiments, the suturing probe (10) can include a recessed portion (23) with the chamber port (20) open to the recessed portion (23) of the suturing probe external surface (13) with the thread carrier (3) operable to pass within the recessed portion (23) of the suturing probe external surface (13) outside of the substrate capture chamber (2). In particular embodiments, the recessed portion (23) of the suturing probe external surface (13) can be arcuate (as shown in the illustrative examples of FIGS. 7 through 9). The arcuate recessed portion (23) of the suturing probe external surface (13) can, but need not necessarily, be configured to allow a tip of a finger (24) to apply force to a substrate (15) to move the substrate toward the substrate capture chamber (2) (as shown in the illustrative example of FIG. 33C).

Now referring primarily to FIGS. 7 through 10, the recessed portion (23) of the suturing probe external surface (13) can include a substantially flat arcuate face (25) in which the chamber port (20) opens to provide a recessed peripheral margin (26) about the chamber port (20). There can be an advantage in a recessed peripheral margin (26) which affords a substantially flat or lessened curvature about the chamber port (20) in that it can increase the surface area of the suturing probe external surface (13) contacting a substrate (15). The increased surface area of the suturing probe external surface (13) can afford a substantial advantage in capture of a substrate (15) in those embodiments in which a reduced chamber pressure (22) can be generated in the substrate capture chamber (2) or can decrease movement of the suturing probe (10) in relation to substrate (15) captured in the substrate capture chamber (2).

Now referring primarily to FIGS. 1, 2, 4, and 10, the chamber port (20) can, but need not necessarily, be disposed in a stadium configuration (27), being a rectangle with semicircles at a pair of opposite sides. The substrate capture chamber (2) can, but need not necessarily, have a chamber bottom (19) in a stadium configuration disposed opposite the chamber port (20) in stadium configuration connected by a substantially vertical chamber sidewall (18).

Figure 34:
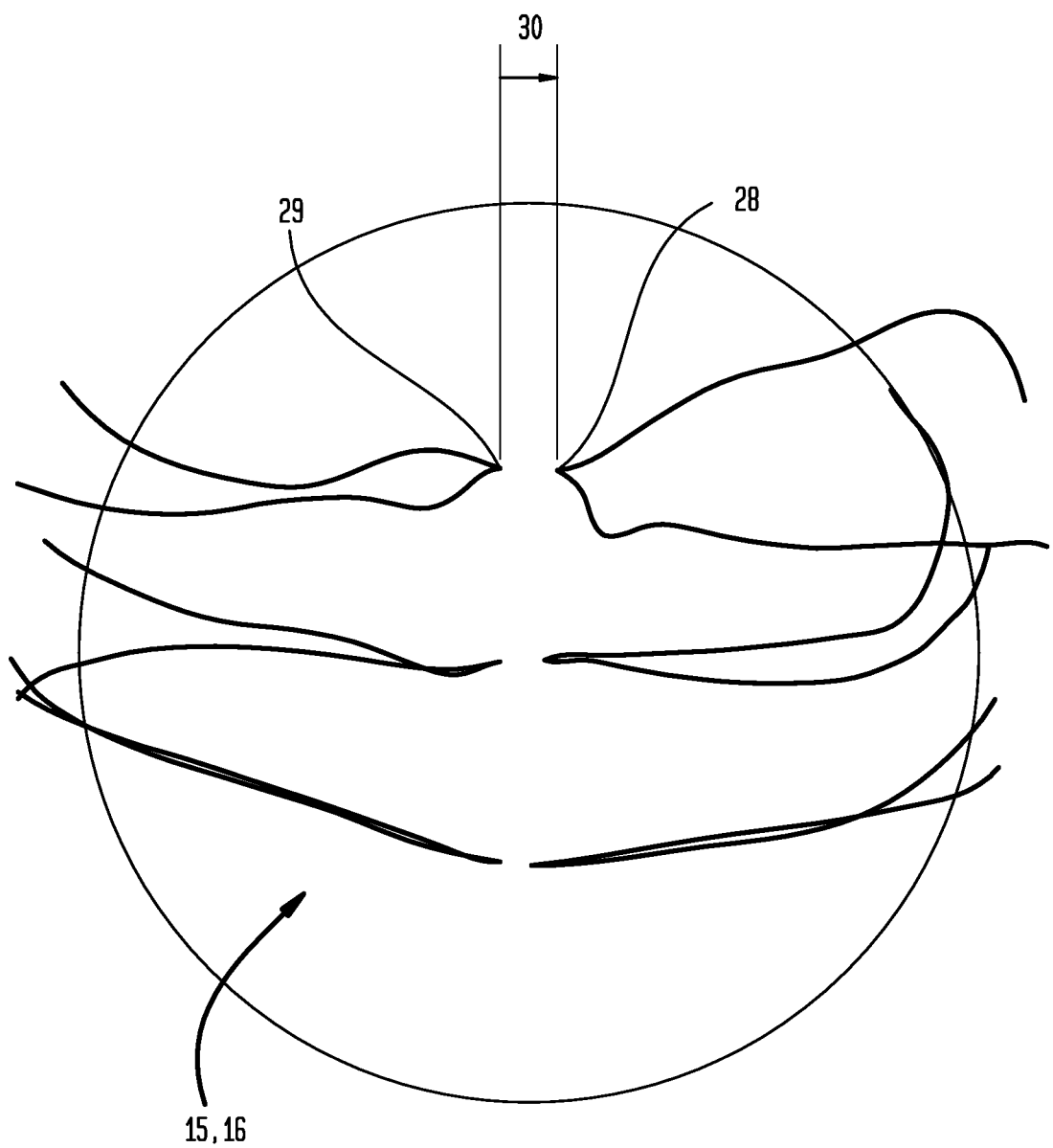
FIG. 34 is an illustration of a plurality of suture purchases obtained by use of the suturing apparatus.

Referring to FIG. 34, there can be an advantage in a substrate capture chamber (2) of stadium configuration (27) in that an increased amount of substrate (15) can be disposed in the substrate capture chamber as compared to a substrate capture chamber having conventionally slotted or substantially circular substrate capture chamber (2) and correspondingly the substrate (15) penetrated by the thread carrier (3) can dispose a thread entry point (28) and a thread withdraw point (29) a greater distance apart (also referred to as the "suture purchase (30)") as compared to conventional slotted or cylindrical suction chambers. The suture purchase (30) generated by use of a stadium configuration (27) can be substantially greater than that obtained using a suction chamber of cylindrical configuration or obtained using a conventional suction chamber of slotted configuration. It may be that the conventional cylindrical configuration draws the substrate into a conical configuration within the conventional cylindrical suction chamber and the conventional needle only penetrates the substrate proximate the apex of the cone. It may be that the conventional slotted suction chamber does not have sufficient volume to dispose the substrate a sufficient distance into the conventional slotted chamber and the conventional needle only penetrates the substrate layers in adjacent relation close to the fold or edges.

Now referring to FIGS. 11 and 12, particular embodiments of the suturing probe can include a substrate capture chamber insert (31). The substrate capture chamber insert (31) can include a substrate capture chamber insert sidewall (32) which joins a substrate capture insert bottom (33) to a substrate capture chamber insert port (34). The substrate capture chamber insert (31) can be removably coupled to the inside of the substrate capture chamber (2) to alter the configuration or volume of the substrate capture chamber (2). The altered configuration or volume corresponding to the substrate capture chamber insert (31) can accordingly increase or decrease the volume of substrate (15) captured in the substrate capture chamber (2) and accordingly adjust the suture purchase (30) (as shown in the illustrative example of FIG. 34). The substrate capture chamber insert (31) can have an insert aperture element (35) disposed to fluidically couple the internal volume of the substrate capture chamber insert (31) and substrate capture chamber insert port (34) with a first longitudinal channel (36) which couples the substrate capture chamber (2) to a vacuum port (37) through which fluid flow (38) passes to regulate the chamber pressure (22) within the substrate capture chamber (2). As shown in the illustrative example of FIG. 12, the substrate capture chamber insert (31) can have a substrate capture chamber insert bottom (33) which between interchangeable embodiments can be disposed at a depth equal to or less than the distance between the substrate capture chamber bottom (19) and the chamber port (20). The substrate capture chamber insert port (34) can have an open area about equal to or less than the open area defined by the chamber port (20). However, this illustrative example is not intended to preclude other configurations of the substrate capture insert (31) which can alter only the chamber sidewall (18), only the chamber port (20), or only the chamber bottom (19), or combinations thereof.

Figure 13:
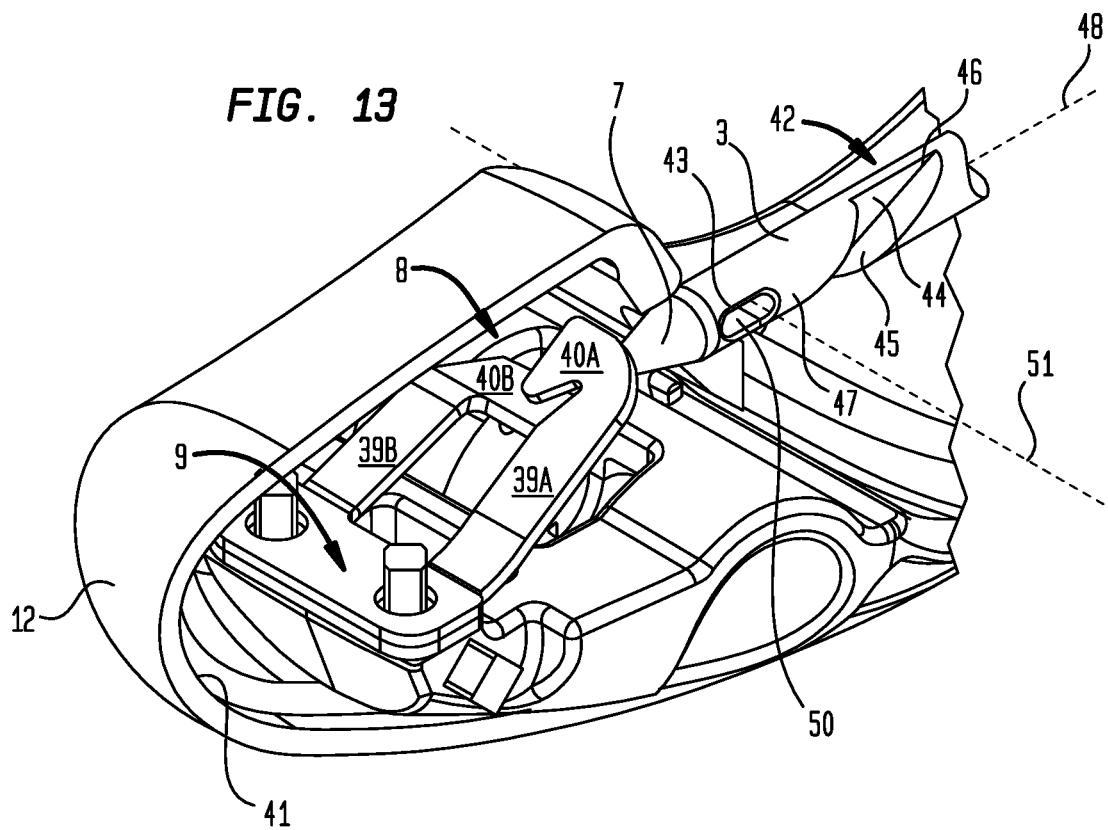
FIG. 13 is an enlarged view of a particular embodiment of a thread carrier and a thread capture assembly showing the position of the thread carrier extended into the thread capture chamber.
Figure 14:
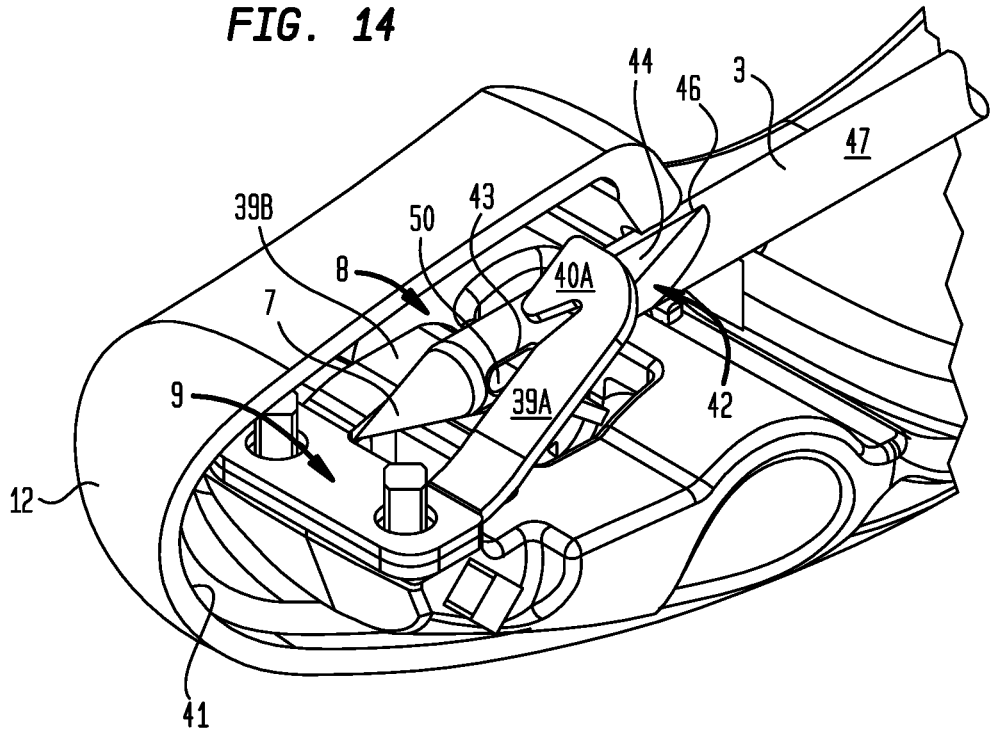
FIG. 14 is an enlarged view of a particular embodiment of a thread carrier and a thread capture assembly showing the position of the thread carrier extended into the thread capture assembly and engaged with the thread capture assembly.
Figure 15:
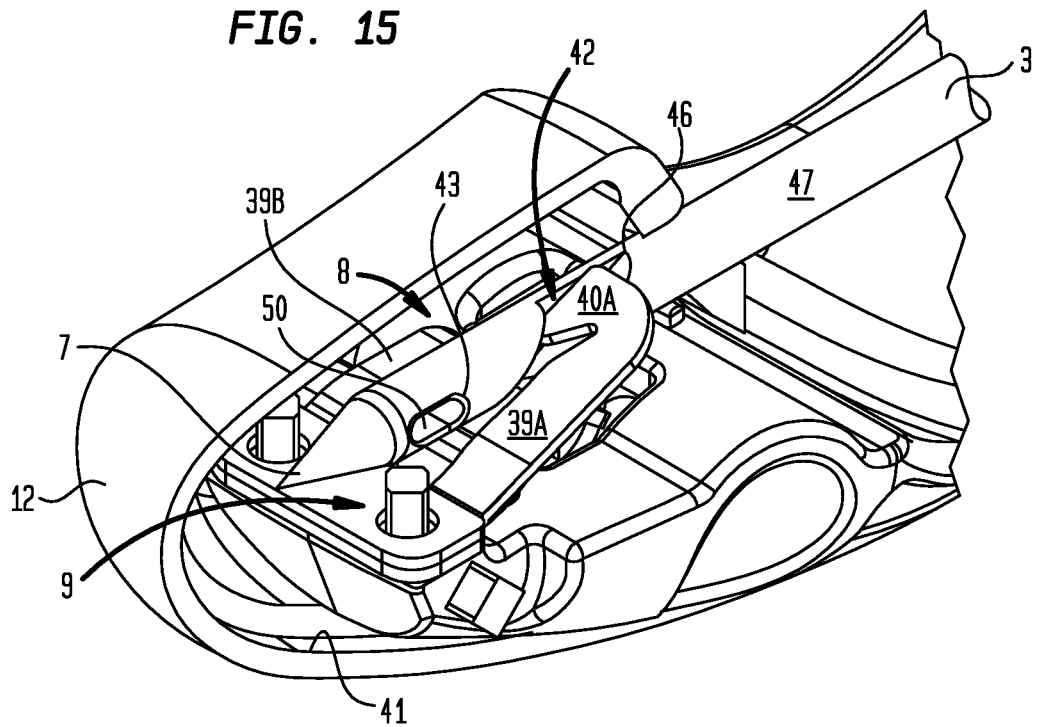
FIG. 15 is an enlarged view of a particular embodiment of a thread carrier and a thread capture assembly showing the position of the thread carrier extended into the thread capture assembly and engaged with the thread capture assembly.
Figure 16:
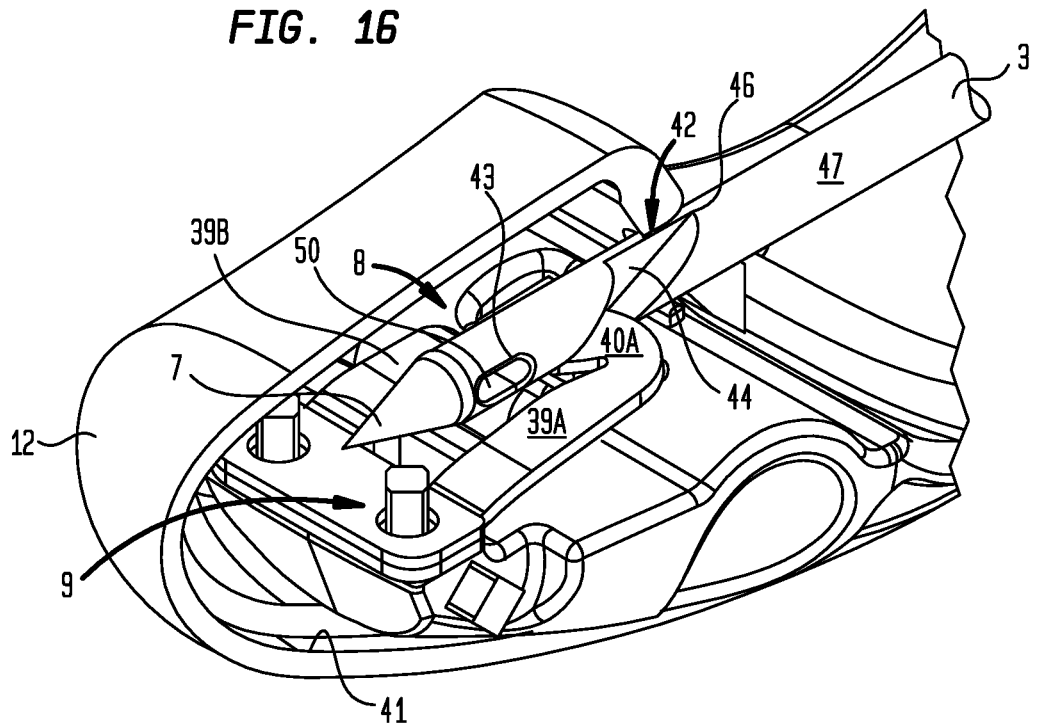
FIG. 16 is an enlarged view of a particular embodiment of a thread carrier and a thread capture assembly showing the position of the thread carrier extended into the thread capture assembly and engaged with the thread capture assembly.
Figure 24:
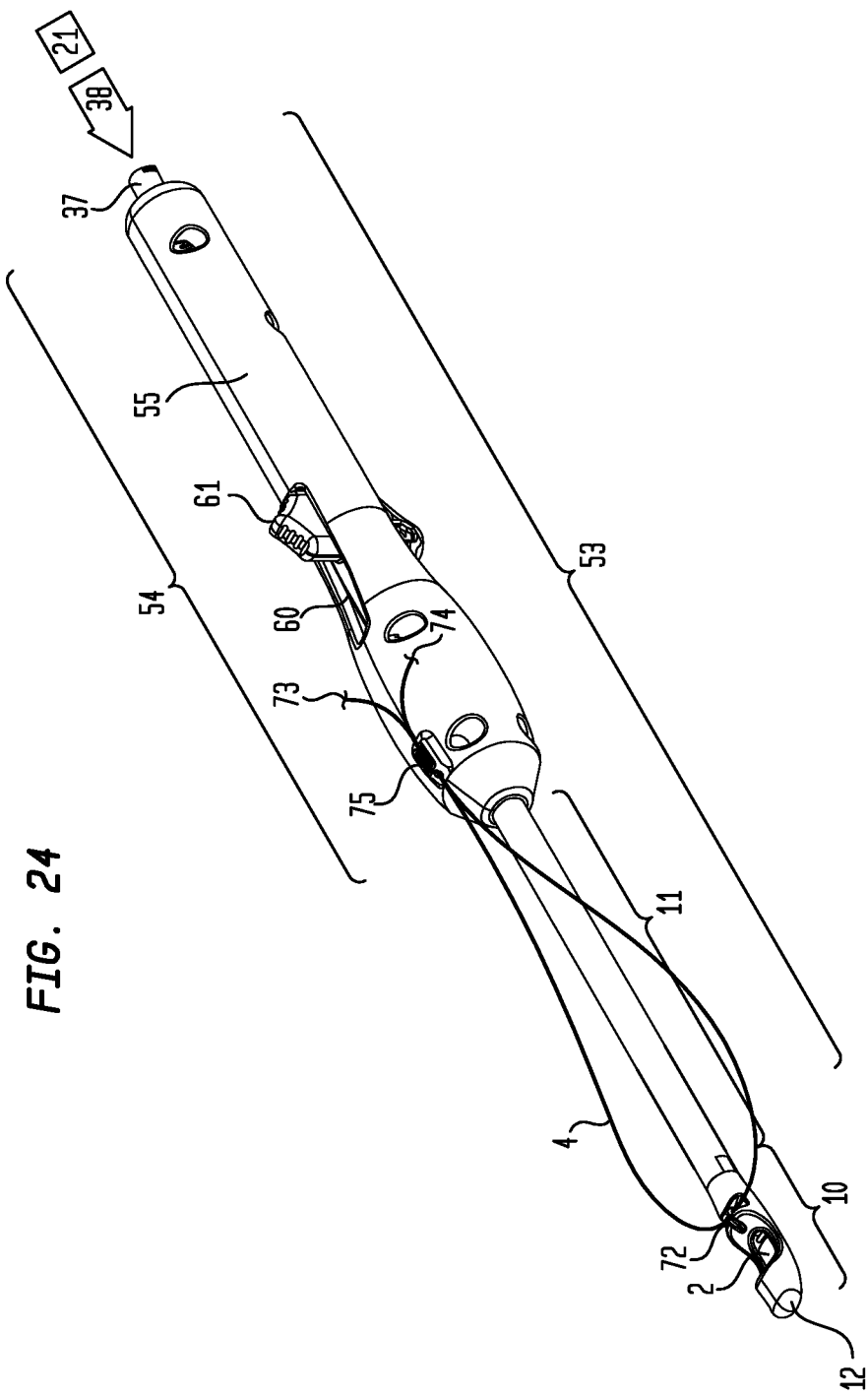
FIG. 24 is a perspective view of a particular embodiment of a suturing apparatus having a thread passing through the thread carrier aperture and disposed in a thread catch.
Figure 25:
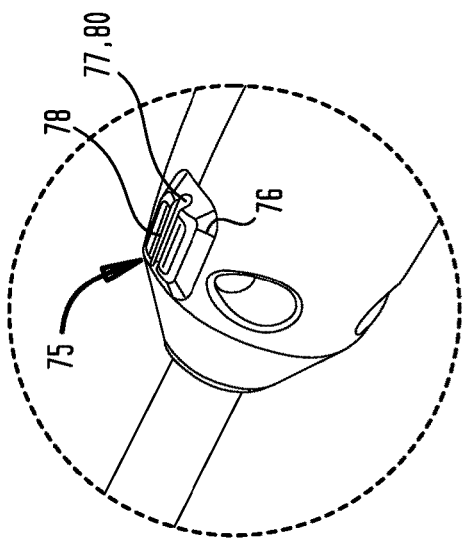
FIG. 25 is an enlarged perspective view of a thread catch as shown in FIG. 1.
Figure 26:
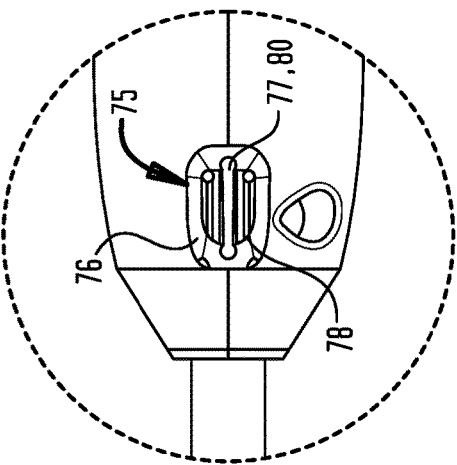
FIG. 26 is an enlarged perspective view of a thread catch as shown in FIG. 1.
Figure 27:
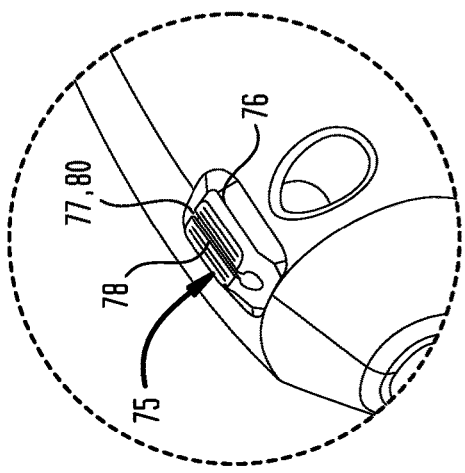
FIG. 27 is an enlarged side view of a particular embodiment of a thread catch.
Figure 28:
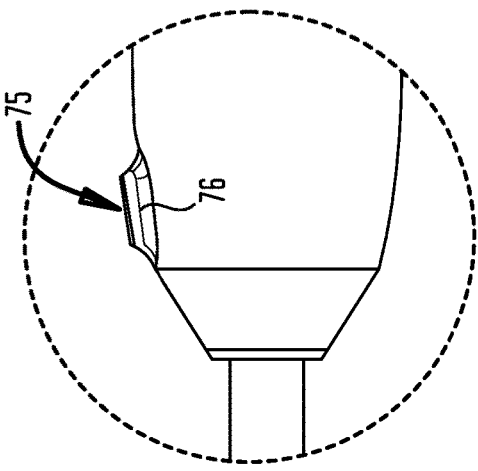
FIG. 28 is an enlarged plan view of a particular embodiment of a thread catch.

Now referring primarily to FIGS. 13 through 16, a thread capture assembly (9) can be disposed in the thread capture chamber (8). The thread capture assembly (9) can include at least one resiliently flexible hook member (39A) correspondingly terminating in at least one hook (40A). The resiliently flexible hook member (39A) can be coupled to the thread capture chamber internal surface (41) to dispose the hook (40A) at a location to engage the thread carrier (3) and flexing the at least one resiliently flexible hook member (39A). As to particular embodiments, the thread capture assembly (9) can include a pair of resiliently flexible hook members (39A)(39B) each correspondingly terminating in one of a pair of hooks (40A)(40B). The pair of resiliently flexible hook members (39A)(39B) can each be coupled to the thread capture chamber internal surface (41) to dispose the pair of hooks (40A)(40B) a distance apart at locations which allow corresponding engagement on opposed sides of the thread carrier (3), thereby flexing each of the pair of resiliently flexible hook members (39A)(39B) (as shown in the example of FIGS. 13 and 14). Upon retraction of the thread carrier (3) from the thread capture chamber (8), the pair of resiliently flexible hook members (39A)(39B) each return toward the unflexed condition correspondingly disengaging each of the pair of hooks (40A)(40B) from the thread carrier (3).

Again, referring primarily to FIGS. 13 through 16, the thread carrier (3) can further include a notch (42) disposed a distance axially from the thread carrier aperture element (43). The notch (42) defines a notch passage (44) between notch passage first and second ends (45)(46) which open on the thread carrier external surface (47). The notch (42) can be disposed angularly across the thread carrier longitudinal axis (48) of the thread carrier (3) to dispose the notch passage first end (45) closer to the thread carrier terminal end (7) and the notch passage second end (46) farther from the thread carrier terminal end (7). The hook (40A) or the pair of hooks (40A)(40B) engage the thread carrier (3) flexing at least one resiliently flexible hook member (39A) or pair of resiliently flexible hook members (39A)(39B) and aligning one of the pair of hooks (40A)(40B) with the notch passage second end (46). Resilient flexure moves the hook (40A) into the notch passage second end (46).

Now referring primarily to FIGS. 17 through 20, the thread carrier (3) can be coupled to the drive member first end (49) and extend axially outward to terminate in a thread carrier terminal end (7). The thread carrier (3) can comprise a slender rod which can, but need not necessarily, taper approaching the thread carrier terminal end (7). The taper can be sufficient to allow the thread carrier (3) to pass through a particular type of substrate (15), and as to particular embodiments, the thread carrier (3) can taper to a sharp point at the thread carrier terminal end (7) to pass through a substrate (15) comprising animal tissue. A thread carrier aperture element (43) can be disposed a distance axially from said thread carrier terminal end (7). The thread carrier aperture element (43) defines a thread carrier aperture (50). As to particular embodiments, the thread carrier aperture (50) can have a thread carrier aperture axis (51) disposed generally orthogonal to the thread carrier longitudinal axis (48) and generally orthogonal to the plane (52) longitudinally bisecting the chamber port (20) (as shown in the cross section of FIG. 18 which longitudinally bisects the chamber port (20) generally orthogonal to the thread carrier aperture axis (51)).

Now referring primarily to FIGS. 1 through 6, embodiments of the suturing apparatus (1) can include a housing (53). The housing (53) can include a handle (54) and a tubular member (11) which outwardly axially extends from the handle (54) terminating in the suturing probe (10). The handle external surface (55) can, but need not necessarily, be configured to be grippingly engaged by the human hand.

Figure 7:
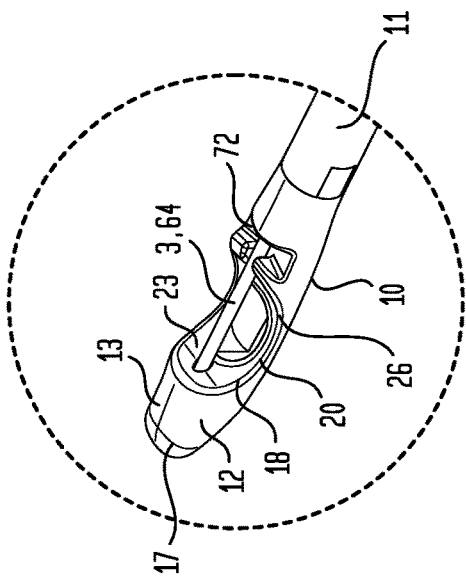
FIG. 7 is an enlarged view of the suturing probe shown in FIG. 1.
Figure 8:
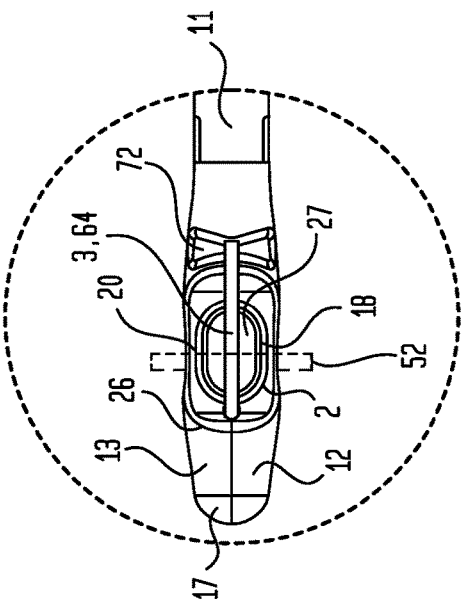
FIG. 8 is an enlarged view of the suturing probe shown FIG. 2.
Figure 9:
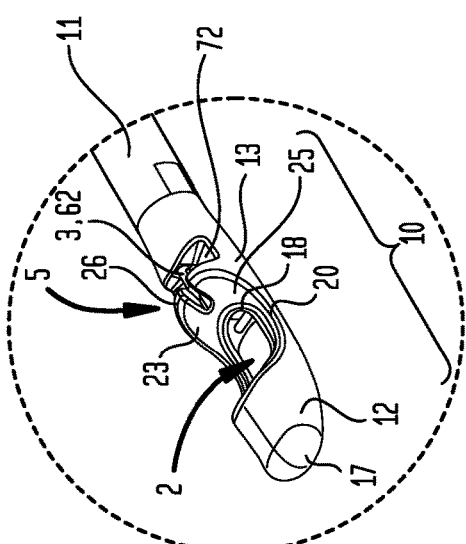
FIG. 9 is an enlarged view of the portion 9 shown in FIG. 3 side elevation view of a particular embodiment of a suturing probe.
Figure 10:
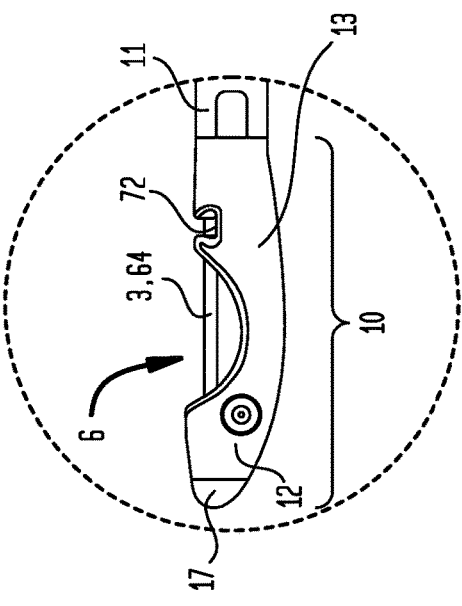
FIG. 10 is an enlarged view of the suturing probe shown in FIG. 10.

Again, referring primarily to FIGS. 17 through 20, the handle (54) can receive in axial sliding engagement a thread carrier driver (56). The thread carrier driver (56) can include an elongate drive member (57) having a length disposed between a drive member first end (49) and a drive member second end (58). The elongate drive member (57) moves axially inside of the handle (54) in response to a drive member actuator (59). As to particular embodiments, a drive member actuator slot (60) can be disposed in the handle (54) and the drive member actuator (59) can be configured to extend through the drive member actuator slot (60) to present a pressible drive member actuator button (61) which upon forcible urging generates corresponding axial movement of the elongate drive member (57) inside of the handle (54). As to particular embodiments, the thread carrier driver (56) can be operated bidirectionally to concurrently reciprocally position the thread carrier terminal end (7) between a thread carrier first position (62) which locates the thread carrier terminal end (7) inside of a second longitudinal channel (63) which opens to the probe external surface (13) outside of the substrate capture chamber (2) and a thread carrier second position (64) with the thread carrier terminal end (7) located in the thread capture chamber (8)(as shown in the examples of FIGS. 7 thorough 10). The second longitudinal channel (63) can be fluidically discrete from the first longitudinal channel (36) coupled to the vacuum source (21). Accordingly, the thread carrier (3) disposed and reciprocally moved in the second longitudinal channel (63) from the first position (62) to the second position (64) outside of the substrate capture chamber (2) does not require a seal engaging the thread carrier (3) to maintain reduced chamber pressure (22) in the substrate capture chamber (2) generated in the first longitudinal channel (36) fluidically coupled to the vacuum source (21).

Figure 2:
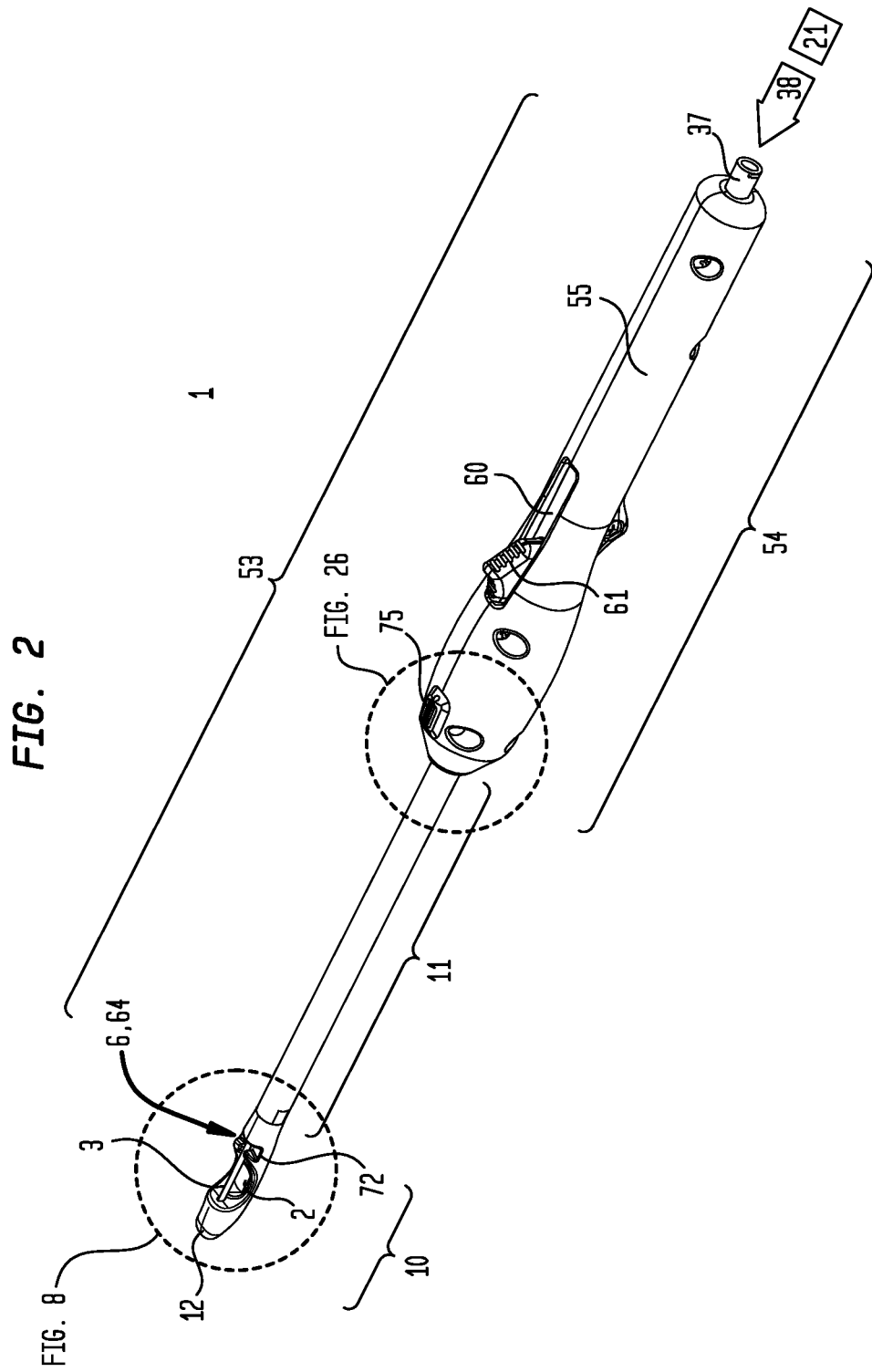
FIG. 2 is a second perspective view of an embodiment of the suturing apparatus having the thread carrier in an extended condition.

Now referring primarily to FIGS. 17 through 19, the housing (53) can be configured to provide a vacuum port (37) opening on the handle external surface (55) (as shown in the examples of FIGS. 1 through 6 and 17 through 19). The vacuum port (37) can be coupled to a vacuum source (21) (as shown in the example of FIGS. 1 and 2). The vacuum source (21) can comprise any of a variety of conventional vacuum or suction pumps. The vacuum source (21) can be operated to generate a reduced chamber pressure (22) in the substrate capture chamber (2).

Now referring primarily to FIGS. 21 through 23, the drive member second end (58) can be coupled to an arrest assembly (65). The arrest assembly (65) can include one or more of an arrest member (66), a prong receiver (67), and a prong (68). The arrest member (66) can have a length disposed between an arrest member first end (69) and an arrest member second end (70). The arrest member first end (69) can be coupled to the thread carrier driver (56). The arrest member second end (70) can have a taper extending toward the arrest member second end (70). Disposed between the arrest member first and second ends (69)(70) can be a prong receiver (67). The prong receiver (67) can engage the prong (68) which can be coupled to the internal surface (71) of the handle (54). The thread carrier driver (56) can be operable to concurrently axially move the thread carrier (3) and the arrest member (66). The arrest member (66) can flex, allowing the prong (68) to disengage the prong receiver (67) when the thread carrier driver (56) operates to move the thread carrier (3) toward the thread carrier second position (64). The arrest member (66) can also flex to allow the prong (68) to traverse along the taper of the arrest member second end (70) toward the prong receiver (67), where the prong (68) can engage the prong receiver (67) when the thread carrier driver (56) operates to move the thread carrier (3) toward the thread carrier first position (62).

Now referring primarily to FIGS. 1 through 11 and 24, a thread (4) can be disposed in the thread carrier aperture element (43). To assist in disposing the thread (4) in the thread carrier aperture element (43), particular embodiments, can include a thread slot (72). The thread slot (72) can be disposed in the suturing probe (10) adjacent the opening of the second longitudinal channel (63) in the suturing probe external surface (13). The location of the thread carrier aperture element (43) disposed in the first position (62) can align with the thread slot (72) to permit a thread (4) to be passed through the thread slot (72) and the thread carrier aperture element (43).

Now referring primarily to FIGS. 24 through 28, in particular embodiments, a method in a suturing apparatus (1) can include passing a first end (73) of a thread (4) through the thread carrier aperture element (43) disposed on the thread carrier (3). In particular embodiments, the method can further include passing the first end (73) of the thread (4) through the thread carrier aperture element (43) while it is aligned with the thread slot (72) disposed in the handle (54). In particular embodiments, the second end (74) of the thread (4) (or both ends of the thread (4)) can be retained in a thread catch (75) disposed on the handle (54). An embodiment of the thread catch (75) can include a thread catch base (76) including a thread catch slot (77) configured to catch and retain a thread (4). In the embodiment, shown in FIGS. 24 through 28, the thread catch (75) can, but need not necessarily include, one or more friction pads (78) disposed in opposed relation about the thread catch slot (77). In particular embodiments, the friction pads (78) can comprise an elastomeric material which increases friction on the thread (4) when disposed in the thread catch slot (77). In particular embodiments, the thread catch (75) can include a thread catch base (76) including a thread catch aperture element (80). The thread catch aperture element (80) can define a thread catch aperture communicating between a distal end of the thread catch (75) and a proximal end of the thread catch (75). The thread (4) can be passed through the thread catch aperture in a distal to proximal direction.

Figure 29:
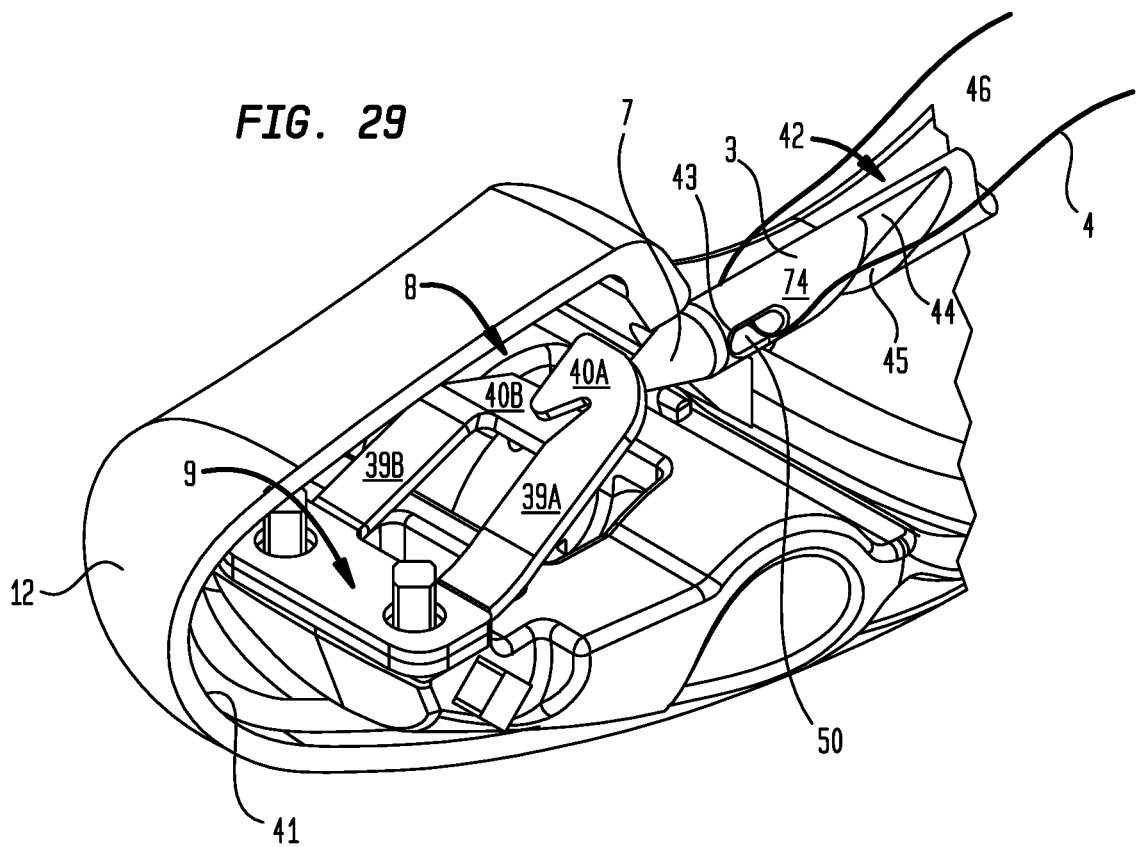
FIG. 29 is an enlarged view of a particular embodiment of a thread carrier and a thread capture assembly showing the position of the thread carrier having a thread carrier extended into the thread capture chamber.
Figure 30:
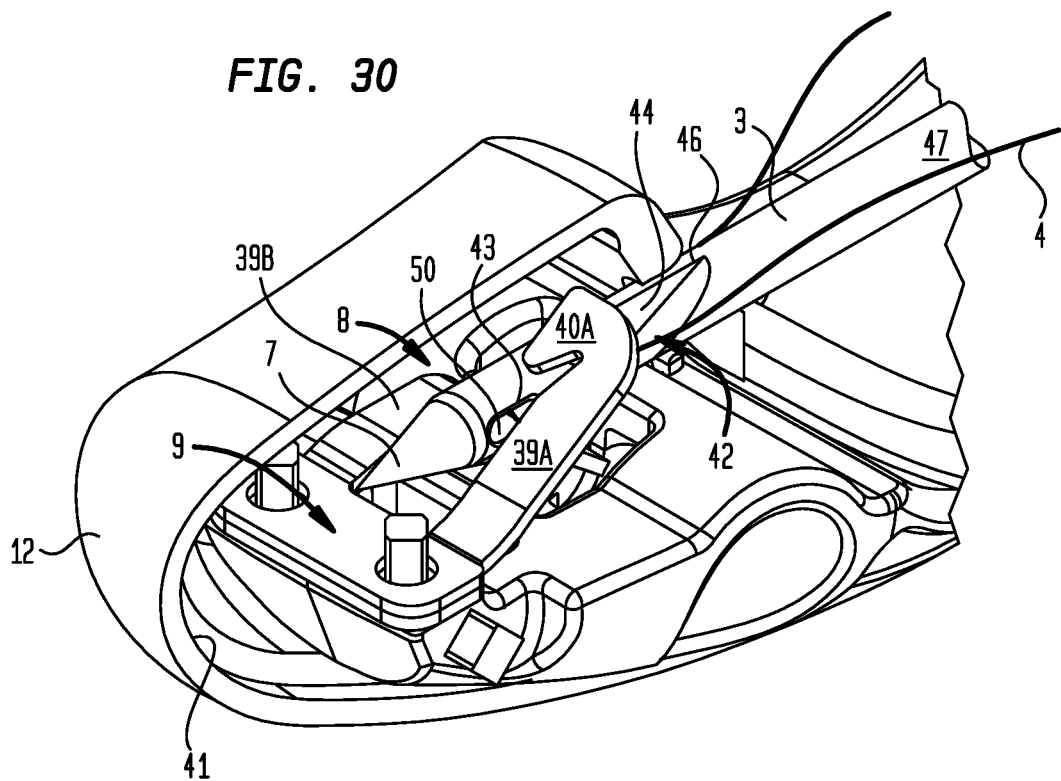
FIG. 30 is an enlarged view of a particular embodiment of a thread carrier and a thread capture assembly showing the position of the thread carrier having a thread carrier engaged with the thread capture assembly.
Figure 31:
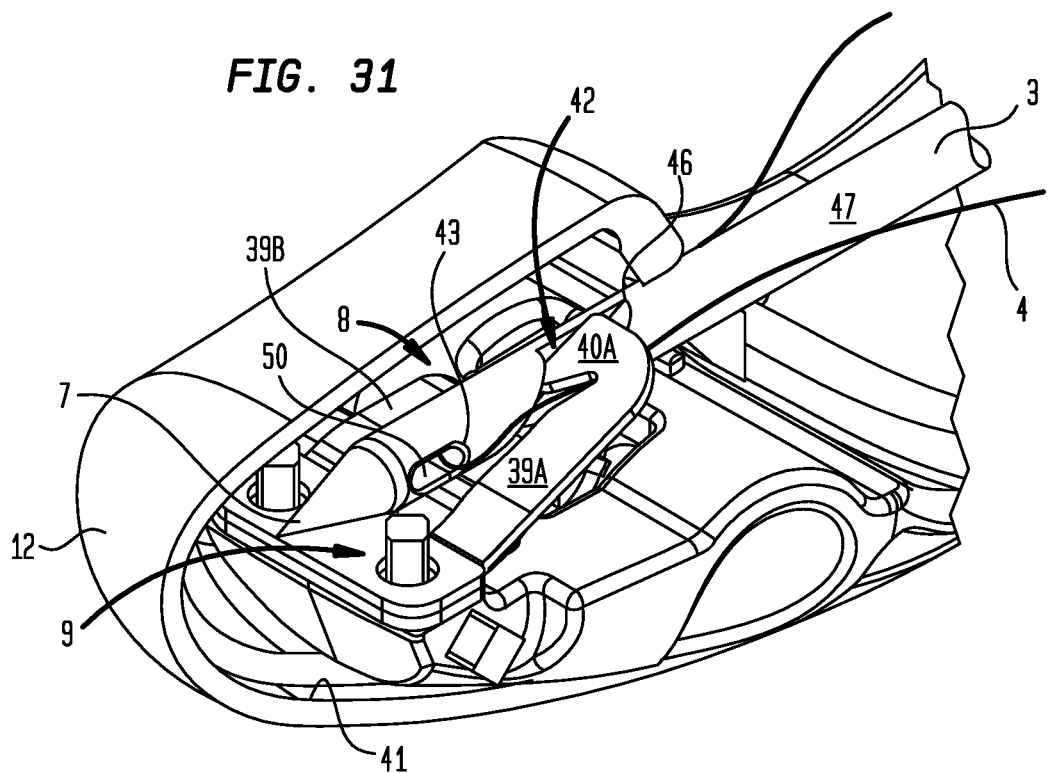
FIG. 31 is an enlarged view of a particular embodiment of a thread carrier and a thread capture assembly showing the position of the thread carrier having engaged with the thread capture assembly.
Figure 32:
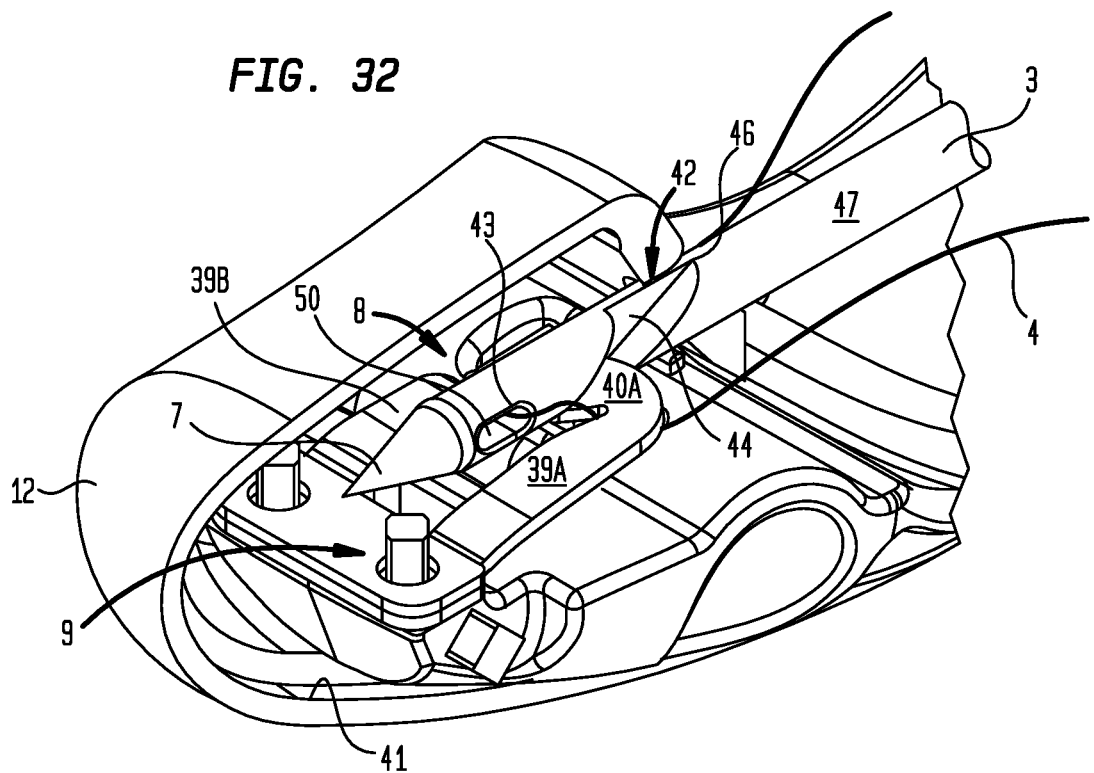
FIG. 32 is an enlarged view of a particular embodiment of a thread carrier and a thread capture assembly showing the position of the thread carrier having a thread captured by the thread capture assembly.

Referring primarily to FIGS. 29 through 32, a method in a suturing apparatus (1) can include driving a thread carrier (3) slidingly engaged to the suturing probe (10) toward the thread capture chamber (8). Slidingly engaging a thread capture assembly (9) disposed in the thread capture chamber (8) with the thread carrier (3) carrying the thread (4). Disposing the thread (4) adjacent at least one resiliently flexible hook member (39A) terminating in a hook (40A). Aligning the hook (40A) with a notch second end (46) of the notch (42) disposed in the thread carrier (3) (as shown in the examples of FIGS. 29 and 30). Driving the thread carrier (3) slidingly engaged to the suturing probe (10) away from the thread capture chamber (8) to move the hook (40A) through the notch passage (44). Capturing the thread (4) on the hook (40A) (as shown in the example of FIGS. 31 and 32).

Figure 33C:
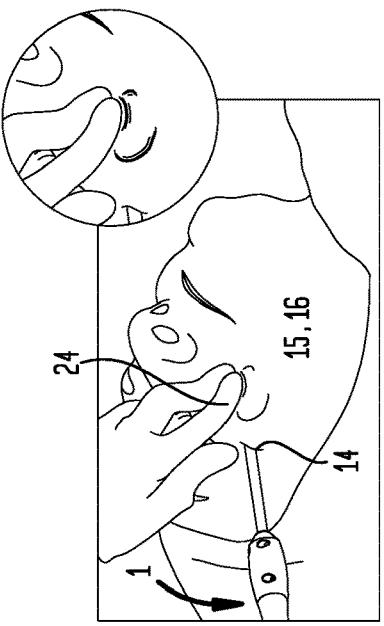
FIG. 33C is a depiction of a particular method of palpating a substrate toward a substrate capture chamber.
Figure 33B:
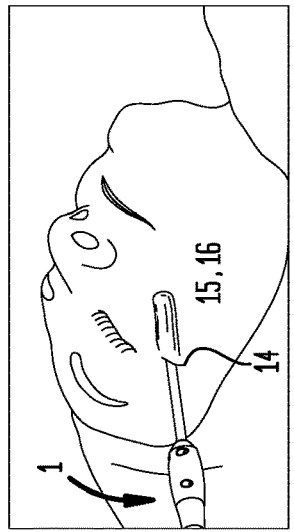
FIG. 33B is a depiction of a particular method of inserting a suturing probe in a body opening.
Figure 33A:
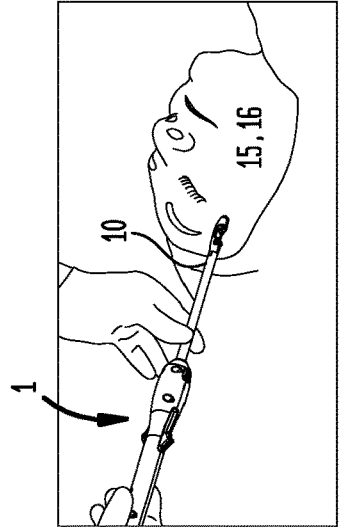
FIG. 33A is a depiction of a particular method of using a suturing apparatus.
Figure 33E:
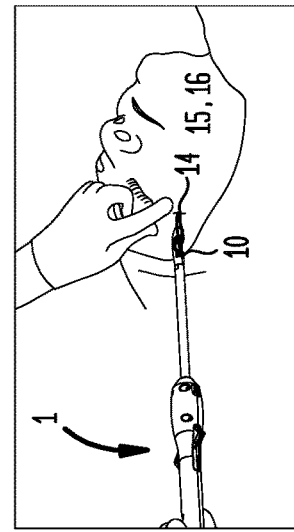
FIG. 33E is a depiction of a particular method of disposing suture loop the substrate and removing a suturing probe from a body opening.
Figure 33D:
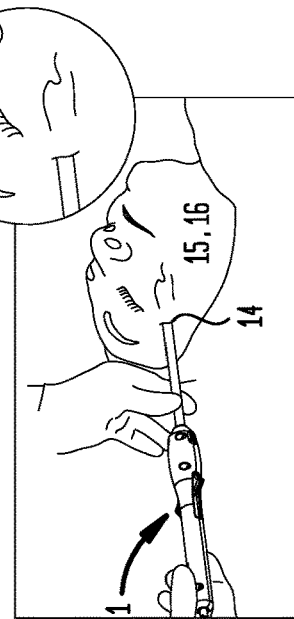
FIG. 33D is a depiction of a particular method of operating the suturing apparatus to drive the thread carrier through a substrate.

Now referring primarily to FIG. 33A through 33E, a method in a suturing apparatus (1) can include passing a first end (73) of a thread (4) through the thread carrier aperture element (43) disposed on the thread carrier (3) (as shown in the example of FIG. 33A). Inserting a suturing probe (10) into a body opening (14) of a substrate (15) (as shown in the example of FIG. 33 B). Forcibly urging the substrate (15) toward a substrate capture chamber (2) disposed in the suturing probe (10) which as to particular embodiments, includes contacting the substrate (15) with a finger (24) or other instrument or device (as shown in the example of FIG. 33C). Capturing the substrate (15) in the substrate capture chamber (2), which can, but need not necessarily, include generating a reduced chamber pressure (22) in the substrate capture chamber (2) by operation of a vacuum source (21) to draw and retain an amount of the substrate (15) in the substrate capture chamber (2). Driving a thread carrier (3) slidably engaged in the suturing probe (10) toward a thread capture chamber (8). Passing the thread carrier (3) carrying the thread (4) through the substrate (15) outside of the substrate capture chamber (2) into the thread capture chamber (8) (as shown in the example of FIG. 33D). Engaging the thread carrier (3) with a thread capture assembly (9) disposed in the thread capture chamber (8). Capturing the thread (4) on the thread capture assembly (9). Reciprocally driving a thread carrier (3) from the thread capture chamber (8) and through the substrate (15) to generate a thread loop in the substrate (15) (as shown in the example of FIG. 33E). In particular embodiments, the methods can further include inserting a substrate capture chamber insert (31) into the substrate capture chamber (2).

With regards to driving a thread carrier (3) in the suturing probe (10) toward a thread capture chamber (8), the method can further include pressing a drive member actuator button (61) extending through the drive member actuator slot (60) in a handle (54) of the suturing apparatus (1). The pressing can generate movement in the thread carrier (3) in a first direction (79) toward the thread capture chamber (8). The movement of the thread carrier (3) in a first direction (79) can pass the thread carrier (3) through the substrate (15) outside of the substrate capture chamber (2) into the thread capture chamber (8) without compromising the integrity of the reduced chamber pressure (22) generated by a vacuum source (21) fluidically coupled to the substrate capture chamber (2). In particular embodiments, the method can further include flexing an arrest assembly (65), thereby disengaging the prong (68) from the prong receiver (67) and advancing the prong (68) along the taper of the arrest member second end (70) and to permit the movement of the thread carrier (3) in the first direction (79).

Now referring primarily to FIG. 34, there can be an advantage in varying the configuration or volume of the substrate capture chamber (2). Various configurations and volumes of the substrate capture chamber (2) can by utilizing a substrate capture chamber insert (31) and the option of utilizing a vacuum source (21) to reduce pressure (22) in the substrate capture chamber (2) correspondingly vary, the suture purchase (30) in the substrate (15, 16) depending on the requirements of the application. In particular embodiments which include a vacuum source (21), reducing pressure (22) in the substrate capture chamber (2) can capture an increased amount of substrate (15) in the substrate capture chamber (2), thereby increasing the suture purchase (30). The suture purchase (30) can be adjusted by the use of a substrate capture chamber insert (31) which varies the volume of the substrate capture chamber (2) available to receive the substrate (15). In other particular embodiments, a substrate capture chamber insert (31) can be utilized without a vacuum source (21), decreasing the suture purchase (30) as opposed to an application which utilizes a vacuum source (21). Thus, by altering the factors of utilizing a substrate capture chamber insert (31) and the utilization of a vacuum source (21), the suture purchase (30) can be increased or decreased depending upon the application.

As can be easily understood from the foregoing, the basic concepts of the present invention may be embodied in a variety of ways. The invention involves numerous and varied embodiments of a mountable carrier and methods for making and using such mountable carrier including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "mount" should be understood to encompass disclosure of the act of "mounting"—whether explicitly discussed or not—and, conversely, were there effectively disclosure of the act of "mounting", such a disclosure should be understood to encompass disclosure of a "mount" and even a "means for mounting." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the mountable carriers herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. An apparatus, comprising:
a suturing probe including a thread capture chamber disposed adjacent a substrate capture chamber, said substrate capture chamber having a chamber sidewall which couples in opposed fixed relation a chamber bottom a distance from a chamber port open to a suturing probe external surface, wherein said chamber port and said chamber bottom each configured as a rectangle with semicircles at opposite ends;
a thread carrier slidingly engaged to said suturing probe, said thread carrier passes outside said substrate capture chamber into said thread capture chamber; and
a substrate capture chamber insert removably coupled inside of said substrate capture chamber, said substrate capture chamber insert having substrate capture chamber insert bottom and a substrate capture chamber insert port open to said external surface of said suturing probe;
wherein said substrate capture chamber insert port and said substrate capture chamber insert bottom are each configured as a rectangle with semicircles at opposite ends.

2. The apparatus of claim 1, wherein said suturing probe external surface includes a recessed portion, said chamber port open to said recessed portion of said suturing probe external surface, said thread carrier passing within said recessed portion of said suturing probe external surface outside of said substrate capture chamber.

3. The apparatus of claim 2, further comprising a thread carrier aperture element disposed proximate a thread carrier terminal end, said thread carrier aperture element defining a thread carrier aperture communicating between opposed aperture openings on said thread carrier external surface.

4. The apparatus of claim 3, further comprising a thread slot disposed in said suturing probe external surface, said thread carrier aperture alignable with said thread slot to pass a thread through said thread carrier aperture.

5. The apparatus of claim 4, wherein said thread carrier aperture having an aperture axis disposed generally orthogonal to a longitudinal axis of said thread carrier.

6. The apparatus of claim 5, wherein said substrate capture chamber insert bottom is disposable at a depth between said chamber bottom and said chamber port.

7. The apparatus of claim 6, wherein said substrate capture chamber insert port has an open area less than an open area defined by said chamber port.

8. An apparatus, comprising:
a suturing probe including a thread capture chamber disposed adjacent a substrate capture chamber, said substrate capture chamber having a chamber port open to a suturing probe external surface; and
a thread carrier slidingly engaged to said suturing probe, said thread carrier passes into said thread capture chamber, said thread carrier including:
a thread carrier aperture element disposed proximate a thread carrier terminal end, said thread carrier aperture element defining a thread carrier aperture communicating between opposed aperture openings on said thread carrier external surface,
a notch disposed in said thread carrier external surface spatially separated from said thread carrier aperture element, said notch defining a notch passage between notch passage first and second ends open on said thread carrier external surface, said notch disposed angularly across a longitudinal axis of said thread carrier to dispose said notch passage first end closer to said thread carrier terminal end and to dispose said notch passage second end farther from said thread carrier terminal end;
a thread capture assembly disposed within said thread capture chamber, said thread capture assembly including at least one resiliently flexible hook member terminating in a hook, said hook disposed in said thread capture chamber engages said thread carrier flexing said at least one resiliently flexible hook member, said hook aligned with said notch second end moves into said notch passage, said hook disengaging said thread carrier by egress from said notch first end.

9. The apparatus of claim 8, wherein said hook disengaging said thread carrier by egress from said notch first end captures thread carried by said thread carrier aperture element to retain a thread loop.

10. The apparatus of claim 9, wherein said thread capture assembly includes a pair of resiliently flexible hook members correspondingly terminating in one of a pair of hooks, said pair of hooks disposed in said thread capture chamber to engage said thread carrier flexing said pair of resiliently flexible hook members, wherein one of said pair of hooks aligned with said notch second end moves into said notch passage, said hook disengaging said thread carrier by egress from said notch first end.

11. The apparatus of claim 10, further comprising a tubular member having a length disposed between a tubular member first end and a tubular member second end, said tubular member first end coupled to said suturing probe, said tubular member second end coupled to a handle.

12. The apparatus of claim 11, further comprising a thread catch disposed on said handle adjacent said tubular member, said thread catch configured to releasably retain said thread.

13. The apparatus of claim 12, further comprising a thread carrier driver coupled to said thread carrier opposite said thread carrier terminal end, said thread carrier responsive to said thread carrier driver to pass outside of said substrate capture chamber into said thread capture chamber.

14. The apparatus of claim 13, further comprising a thread carrier driver actuator extending through a drive member actuator slot in said handle to provide a pressible drive member actuator button.

15. The apparatus of claim 14, further comprising an arrest assembly coupled to said thread carrier driver, said arrest assembly including:
  an arrest member having a length disposed between an arrest member first end coupled to said thread carrier driver and an arrest member second end having a taper extending toward said arrest member second end;
  a prong receiver disposed between said arrest member first and second ends;
  a prong coupled to an internal surface of said handle, said prong engageable with said prong receiver;
  said thread carrier driver operable to concurrently axially move said thread carrier and said arrest member, said arrest member flexes to allow said prong to disengage said prong receiver, said prong traversing along said taper of said arrest member second end, thereby disposing said thread carrier in a first thread carrier position inside of said thread capture chamber.

16. The apparatus of claim 15, wherein said arrest member flexes to allow said prong to traverse along said taper of said arrest member second end toward said prong receiver, said prong engaging said prong receiver to dispose in a second thread carrier position outside of said thread capture chamber.

17. The apparatus of claim 16, further comprising a vacuum source coupled to said substrate capture chamber.

18. The apparatus of claim 17, further comprising a discrete first longitudinal channel coupled between said vacuum source and said substrate capture chamber; and
  a discrete second longitudinal channel disposed in said tubular member capable of permitting said thread carrier to reciprocally axially move, said second longitudinal channel being devoid of a seal.

* * * * *